US006811766B1

(12) United States Patent
Eriksen et al.

(10) Patent No.: US 6,811,766 B1
(45) Date of Patent: Nov. 2, 2004

(54) ULTRASOUND IMAGING WITH CONTRAST AGENT TARGETED TO MICROVASCULATURE AND A VASODILATOR DRUG

(75) Inventors: Morten Eriksen, Oslo (NO); Jonny Østensen, Oslo (NO); Sigmund Frigstad, Trondheim (NO); Pål Rongved, Oslo (NO)

(73) Assignee: Amersham Health AS, Oslo (NO)

(*) Notice: Subject to any disclaimer, the term of this patent is extended or adjusted under 35 U.S.C. 154(b) by 0 days.

(21) Appl. No.: 09/553,048

(22) Filed: Apr. 20, 2000

Related U.S. Application Data

(63) Continuation of application No. PCT/GB98/03155, filed on Oct. 21, 1998.
(60) Provisional application No. 60/071,710, filed on Jan. 16, 1998, and provisional application No. 60/084,879, filed on May 8, 1998.

(30) Foreign Application Priority Data

Oct. 21, 1997 (GB) .............................. 9722224
Apr. 28, 1998 (GB) .............................. 9809099

(51) Int. Cl.$^7$ ................................ A61B 8/00
(52) U.S. Cl. ................ 424/9.52; 424/9.5; 600/458
(58) Field of Search .................. 424/9.5, 9.51, 424/9.52; 600/441, 458

(56) References Cited

U.S. PATENT DOCUMENTS

| | | | | |
|---|---|---|---|---|
| 5,117,830 A | * | 6/1992 | McAfee et al. | 128/654 |
| 5,639,443 A | * | 6/1997 | Schutt et al. | 424/9.52 |
| 5,846,517 A | * | 12/1998 | Unger | 424/9.52 |
| 5,955,055 A | * | 9/1999 | Lees et al. | 424/1.69 |

FOREIGN PATENT DOCUMENTS

| | | |
|---|---|---|
| WO | WO 98 40285 A | 12/1996 |
| WO | WO 98 10799 A | 3/1998 |
| WO | WO 98 17324 A | 4/1998 |
| WO | WO 98 18498 A | 5/1998 |
| WO | WO 98 18501 A | 5/1998 |

OTHER PUBLICATIONS

Porter T.R. et al., "Detection of Mycocardial Perfusion Abnormalities During Dobutamine and Adenosine Stress Echocardiography with Transient Myocardial Contrast Imaging After Minute Quantities of Intravenous Perfluoro-carbon–Exposed Sonicated Dextrose Albumin", Journal American Society of Echocardiography, Nov. 1996, XP002091328.

Leischik R. et al., "Contrast Echocardiography for Assessment of Myocardial Perfusion", HERZ, 1997, XP002091029.

Vandenberg et al., "Myocardial Risk Area and Peak Gray Level Measurement by Contrast Echocardiography: Effect of Microbubble Size and Concentration, Injection Rate, and Coronary Vasodilation", American Heart Journal, 1988, XP002091028.

Iliceto S. et al., "Myocardial Contrast Echocardiography in Acute Myocardial Infarction. Pathophysiological Background and Clinical Applications", European Heart Journal, 1996, XP002091306.

Firschke C. et al., "Myocardial Contrast Echocardiograhy in Acute Myocardial Infarction Using Aortic Root Injections of Microbubbles in Conjunction with Harmonic Imaging: Potential Application in the Cardiac Catheterization Laboratory", Journal American College Cardiology, Jan. 1997, XP002091413.

* cited by examiner

Primary Examiner—Michael G. Hartley
(74) Attorney, Agent, or Firm—Li Cai

(57) ABSTRACT

A combined preparation comprising: i) an ultrasound contrast agent capable of accumulation in tissue microvasculature; and ii) a pharmacologically effective amount of a vasodilator drug may be used in perfusion imaging, especially of the myocardium. The contrast agent accumulates in tissue in concentrations related to the regional rate of tissue perfusion, and the vasodilator drug enhances distinction between normally perfused and underperfused tissue.

7 Claims, No Drawings

ULTRASOUND IMAGING WITH CONTRAST AGENT TARGETED TO MICROVASCULATURE AND A VASODILATOR DRUG

This application is a continuation of pending international application number PCT/GB98/03155 filed Oct. 21, 1998 (of which the entire disclosure of the pending, prior application is hereby incorporated by reference), which itself is a continuation-in-part of U.S. provisional applications Nos. 60/071,710, filed Jan. 16, 1998 and 60/084,879, filed May 8, 1998.

This invention relates to ultrasound imaging, more particularly to use of ultrasound imaging in visualising tissue perfusion, i.e. blood flow per unit of tissue mass, in particular cardiac perfusion.

It is well known that contrast agents comprising dispersions of gas microbubbles are particularly efficient backscatterers of ultrasound by virtue of the low density and ease of compressibility of the microbubbles. Such microbubble dispersions, if appropriately stabilised, may permit highly effective ultrasound visualisation of, for example, the vascular system and tissue microvasculature, often at advantageously low doses.

Measurements of tissue perfusion are of importance in, for example, tumour detection, tumour tissue typically having different vascularity from healthy tissue, and studies of the myocardium, e.g. to evaluate the blood supply thereto. Whilst contrast agent detection using current ultrasound imaging techniques may provide information as to whether particular organs or regions thereof are perfused or not, it does not readily permit quantification of levels of perfusion. Such information, which is useful in assessing whether a patient is at risk owing to low perfusion and so may benefit from preventative methods and/or treatment, must currently be obtained using radioisotopic imaging techniques such as scintigraphy, positron emission tomography or single photon emission computed tomography. These techniques all involve injection of radioactive substances, with potential safety risks for both the patient and medical staff, and use of expensive imaging equipment; this inevitably prohibits their widespread use.

It is known from radionucleide cardiac imaging that patients may be subjected to physical or pharmacological stress in order to enhance the distinction, and thus the difference in imaging intensities, between normally perfused myocardium and any myocardial regions supplied by stenotic arteries. Such stress induces vasodilatation and increased blood flow in healthy myocardial tissue, whereas blood flow in underperfused tissue supplied by a stenotic artery is substantially unchanged since the capacity for arteriolar vasodilatation is already exhausted by inherent autoregulation seeking to increase the restricted blood flow.

The application of stress as physical exercise or pharmacologically by administration of adrenergic agonists may cause discomfort such as chest pains in patient groups potentially suffering from heart disease, and it is therefore preferable to enhance the perfusion of healthy tissue by administration of a vasodilating drug.

The present invention is based on the finding that ultrasound contrast agents capable of accumulation in tissue microvasculature may be used in perfusion imaging, especially of the myocardium, when coadministered with a pharmacologically effective amount of a vasodilating drug. Because such contrast agents will accumulate in tissue in concentrations related to the regional rate of tissue perfusion, ultrasound imaging modalities such as conventional or harmonic B-mode imaging where the display is derived from return signal intensities will provide images which may be interpreted as perfusion maps in which the displayed signal intensity is a function of local perfusion. This is in contrast to images obtained using free-flowing contrast agents, where the regional concentration of contrast agent and corresponding return signal intensity depend on the actual blood content rather than the rate of perfusion of local tissue.

A disadvantage of existing radionucleide cardiac imaging techniques is that the uptake of radionucleide tracers such as thallium 201 and technetium sestamibi is limited by low contact time between tracer and tissue and so may require maintenance of vasodilatation for the whole period of blood pool distribution for the tracer (e.g. 4–6 minutes for thallium scintigraphy) to ensure optimum effect. Accumulative ultrasound contrast agents used in accordance with the present invention, on the other hand, do not suffer such diffusion or transport limitations and, especially where accumulation occurs through a process of physical entrapment, may undergo highly efficient retention in tissue microvasculature. The period of vasodilatation needed to achieve cardiac or other perfusion imaging in accordance with the invention may therefore be short, for example less than one minute; this will reduce the duration of any possible discomfort caused to patients by administration of vasodilator drugs.

In accordance with one embodiment of the invention there is provided a combined preparation for use as a contrast agent in ultrasound perfusion imaging, especially cardiac perfusion imaging, said preparation comprising:

i) an ultrasound contrast agent capable of accumulation in tissue microvasculature, e.g. of the myocardium; and ii) a pharmacologically effective amount of a vasodilator drug.

According to a further embodiment of the invention there is provided a method of generating enhanced perfusion images, especially cardiac perfusion images, of a human or non-human animal subject which comprises the steps of:

i) injecting an ultrasound contrast agent capable of accumulation in tissue microvasculature, e.g. of the myocardium, into the vascular system of said subject;

ii) coadministering a pharmacologically effect amount of a vasodilator drug; and iii) generating an ultrasound image representing perfusion of a target organ or tissue, especially the myocardium.

Representative vasodilator drugs useful in accordance with the invention include endogenous/metabolic vasodilators such as lactic acid, adenosine triphosphate, adenosine diphosphate, adenosine monophosphate, adenosine, nitric oxide and agents causing hypercapnia, hypoxia/hypoxemia or hyperemia; phosphodiesterase inhibitors such as dipyridamole and sildenafil; sympathetic activity inhibitors such as clonidine and methyldopa; smooth muscle relaxants such as papaverine, hydralazine, dihydralazine and nitroprusside; beta receptor agonists such as dopamine, dobutamine, arbutamine, albuterol, salmeterol and isoproterenol; alpha receptor antagonists such as doxazosin, terazosin and prazosin; organic nitrates, such as glyceryl trinitrate, isosorbide dinitrate and isosorbide mononitrate; angiotensin converting enzyme (ACE) inhibitors such as benazepril, captopril, enalapril, fosinopril, lisinopril, quinapril and ramipril; angiotensin II antagonists (or AT1 receptor antagonists) such as valsartane, losartan and candesartan; calcium channel blockers such as amlodipine, nicardipine, nimodipine, felodipine, isradipine, diltiazem, verapamil and nifedipine; prostaglandins such as alprostadil; and endothelium-dependent vasodilators.

In view of the fact that the required vasodilatation may need only to be short lasting, adenosine is a particularly useful vasodilating drug, being both an endogenous substance and having a very short-lasting action as evidenced by a blood pool half-life of only a few seconds. Vasodilatation will accordingly be most intense in the heart, since the drug will tend to reach more distal tissues in less than pharmacologically active concentrations, and may result in coronary blood flow in healthy myocardial tissue increasing by more than 400%. It will be appreciated that because of this short half-life, repeated injection or infusion of adenosine may be necessary during cardiac imaging in accordance with the invention; by way of example, an initial administration of 150 μg/kg of adenosine may be made substantially simultaneously with administration of the contrast agent, followed 10 seconds later by slow injection of a further 150 μg/kg of adenosine, e.g. over a period of 20 seconds.

One category of accumulative contrast agents useful in accordance with the invention comprise gas-containing contrast agent preparations which promote controllable and temporary growth of the gas phase in vivo following administration owing to the presence of a diffusible component capable of inward diffusion into the dispersed gas phase to promote temporary growth thereof, thereby acting as deposited perfusion tracers. Such compositions therefore comprise:

i) an injectable aqueous medium having gas dispersed therein; and ii) a composition comprising a diffusible component capable of diffusion in vivo into said dispersed gas so as at least transiently to increase the size thereof. Accumulative contrast agents of this type are extensively described in WO-A-9817324, the contents of which are incorporated herein by reference.

The dispersed gas in such a preparation may, for example, comprise air, nitrogen, oxygen, carbon dioxide, hydrogen, an inert gas, a sulphur fluoride, selenium hexafluoride, an optionally halogenated silane, an optionally halogenated low molecular weight hydrocarbon (e.g. having a molecular weight such that it is substantially or completely in gaseous form at the normal human body temperature of 37° C.), a ketone, an ester or a mixture of any of the foregoing. The use of perfluorinated gases, for example sulphur hexafluoride, perfluorinated ketones, perfluorinated ethers and perfluorocarbons, including perfluoroalkanes such as a perfluoropropane, perfluorobutane or perfluoropentane, perfluoroalkenes and perfluorocycloalkanes, may be particularly advantageous in view of the recognised high stability in the bloodstream of microbubbles containing such gases.

The dispersed gas may, for example, be in the form of microbubbles stabilised (e.g. at least partially encapsulated) by a coalescence-resistant surface membrane such as gelatin, a filmogenic protein (e.g. an albumin such as human serum albumin), a polymer material, a non-polymeric and non-polymerisable wall-forming material or a surfactant (e.g. a phospholipid, preferably such that at least 75% of the surfactant material comprises molecules individually bearing net overall charge, for example negative charge as in phosphatidylserines, phosphatidylglycerols, phosphatidylinositols, phoaphatidic acids and cardiolipins).

The diffusible component may advantageously be dispersed in an aqueous carrier liquid in the form of an oil-in-water emulsion or microemulsion and may, for example, comprise an aliphatic ether such as diethyl ether; a polycyclic oil or alcohol such as menthol, camphor or eucalyptol; a heterocyclic compound such as furan or dioxane; an aliphatic hydrocarbon or cycloaliphatic hydrocarbon, e.g. containing up to 7 carbon atoms; or halogenated low molecular weight hydrocarbon, e.g. contaning up to 7 carbon atoms. The use of perfluorocarbons, e.g. a perfluoroalkane such as perfluoropentane or perfluorohexane, a perfluoroalkene, a perfluorocycloalkane such as perfluorodimethylcyclobutane, or a perfluorinated alcohol may be advantageous.

Where the diffusible component is formulated as an emulsion it may advantageously be stabilised using a phospholipid surfactant, e.g. as described above in connection with the stabilisation of gas dispersions.

The diffusible component may be administered by any appropriate route, for example cutaneously, subcutaneously, intramuscularly, intravenously or by inhalation.

A further class of accumulative ultrasound contrast agent which may be used in accordance with the invention comprises phase shift colloids such as are described in WO-A-9416739, the contents of which are incorporated herein by reference. Such agents comprise colloidal dispersions of the liquid-in-liquid type in which the dispersed liquid has a boiling point below the body temperature of the subject to be imaged, so that it may volatilise to form expanding gas microbubbles following administration. Representative examples of such agents include emulsions of volatile hydrocarbons, particularly perfluorocarbons such as perfluoropentane, for example stabilised with surfactants such as phospholipids, e.g. as described above in relation to emulsions of diffusible components.

A still further class of accumulative ultrasound contrast agents which may be used in accordance with the invention comprises targetable ultrasound contrast agents having affinity for sites and/or structures within tissue microvasculature. Such targetable agents will typically comprise (i) a reporter moiety capable of interacting with ultrasound irradiation to generate a detectable signal; (ii) one or more vectors having affinity for particular target sites and/or structures; and (iii) one or more linkers connecting said reporter and vector(s), in the event that these are not directly joined.

Reporters which may be useful in such targetable agents include any of the gas-containing systems hereinbefore described in the context of gas-containing ultrasound contrast agent formulations.

The targetable agents may, for example, comprise vectors which have affinity for normal or activated endothelial cells such that they target the vascular endothelium and become at least transiently concentrated on the walls of blood vessels. Activation of endothelium may for example be caused by microbial infections, infarcts or ischemia. Representative vectors in this context include ligands for cell adhesion molecules, for instance proteins or carbohydrate-containing molecules, as well as cell adhesion molecules themselves where these have corresponding ligands on endothelial cell surfaces.

Examples of cell adhesion molecules occuring on activated endothelial cell surfaces include integrins, such as ICAM-1, most of which bind the Arg-Gly-Asp (RGD) amino acid sequence. Specific cell adhesion molecules may occur, or occur in elevated amounts, in relation to the formation of thrombi, for instance blood coagulation factors, e.g. such as Factor XIII, and glycoproteins such as GP IIb/IIIa on activated blood platelets. Thrombi may be targeted by platelet binding peptides such as PLYKKIIKKLLES, NDGDFEEIPEEYLQ and GPRG. Atherosclerotic plaques may be targeted by specific peptides such as YRALVDTLK, YAKFRETLEDTRDRMY and RALVDTEFKVKQEAGAK. Damaged vessel walls may expose targetable myocyte-specific molecules. Angiogenesis may cause elevation of receptors to VEGF and tumours may be targeted by cholecystokinin, alpha-melanocyte-stimulating hormone, heat stable enterotoxin 1, vasoactive intestinal peptide, $\alpha_v\beta_3$ (vitronectin receptor), uPAR (urokinase plasminogen activator receptor), oncofetal fibronectin, synthetic alpha-M2 peptide from the third heavy chain complementarity-determining region and analogues thereof. Further references to this technology, e.g. in targeting to fibrin, thrombi and atherosclerotic areas are found in publications by Alkanonyuksel, H et al. in J. Pharm. Sci. (1966) 85 (5), 486–490; J. Am. Coll. Cardiol. (1996) 27 (2) Supl A, 298A; and Circulation, 68 Sci. Sessions; Anaheim, 13–16 Nov. 1995.

Other vectors which may be used include proteins and peptides which bind to cell-surface proteoglycans. Such proteoglycans, which are complexes of proteins and sulphated polysaccharides, are found on most cells, including endothelial cells, and contribute to the negative surface charge exhibited by all eukaryotic cells. This charge may be exploited in accordance with this embodiment of the invention by using vectors which will interact electrostatically with the endothelial surface, for example vectors comprising cationic lipids.

Linking of a reporter unit to a desired vector or vectors may be achieved by covalent or non-covalent means, usually involving interaction with one or more functional groups located on the reporter and/or the vector(s). Examples of chemically reactive functional groups which may be employed for this purpose include amino, hydroxyl, sulfhydryl, carboxyl and carbonyl groups, as well as carbohydate groups, vicinal diols, thioethers, 2-aminoalcohols, 2-aminothiols, guanidinyl, imidazolyl and phenolic groups. Covalent coupling of reporter and vector(s) may therefore be effected using linking agents containing reactive moieties capable of reaction with such functional groups, e.g. as is well known in the art.

Various vectors and linking agents which it may be useful to adopt in targetable ultrasound contrast agents in accordance with this embodiment of the invention are disclosed in EP-A-0727225 and WO-A-9640285. Suitable vectors, linkers etc. may also be selected from the wide range of known vectors and linking groups summarised in WO-A-9818495, WO-A-9818498, WO-A-9818500 and WO-A-9818501. The contents of all these documents are incorporated herein by reference.

Representative ultrasound imaging techniques which may be useful in accordance with the invention include fundamental B-mode imaging; harmonic B-mode imaging including reception of sub-harmonics and the second and higher harmonics; tissue Doppler imaging, optionally including selective reception of fundamental, harmonic or sub-harmonic echo frequencies; colour Doppler imaging, optionally including selective reception of fundamental, harmonic or sub-harmonic echo frequencies; power Doppler imaging, optionally including selective reception of fundamental, harmonic or sub-harmonic echo frequencies; power or colour Doppler imaging utilising loss of correlation or apparent Doppler shifts caused by changes in the acoustical properties of contrast agent microbubbles such as may be caused by spontaneous or ultrasound-induced destruction, fragmentation, growth or coalescense; pulse inversion imaging, optionally including selective reception of fundamental, harmonic or sub-harmonic echo frequencies, and also including techniques wherein the number of pulses emitted in each direction exceeds two; pulse inversion imaging utilising loss of correlation caused by changes in the acoustical properties of contrast agent microbubbles such as may be caused by spontaneous or ultrasound-induced destruction, fragmentation, growth or coalescense; pulse pre-distortion imaging, e.g. as described in 1997 IEEE Ultrasonics Symposium, pp. 1567–1570; and ultrasound imaging techniques based on comparison of echoes obtained with different emission output amplitudes or waveform shapes in order to detect non-linear effects caused by the presence of gas bubbles.

The following non-limitative examples serve to illustrate the invention.

Preparation 1 a) Perfluorobutane Gas Dispersion

Hydrogenated phosphatidylserine (100 mg) in a 2% solution of propylene glycol in purified water (20 ml) was heated to 80° C. for 5 minutes and the resulting dispersion was allowed to cool to room temperature overnight. 1 ml portions were transferred to 2 ml vials, the headspace above each portion was flushed with perfluorobutane gas, and the vials were shaken for 45 seconds using an Espe CapMix® mixer for dental materials, yielding milky white microbubble dispersions with a volume median diameter of 5.0 $\mu$m, measured using a Coulter Counter (all Coulter Counter measurements were made at room temperature using an instrument fitted with a 50 $\mu$m aperture and having a measuring range 1–30 $\mu$m; Isoton II was used as electrolyte).

b) Dispersion of Lyophilised Perfluorobutane Gas Dispersion

A sample of the milky white dispersion prepared as in (a) above was washed three times by centrifugation and removal of the infranatant, whereafter an equal volume of 10% sucrose solution was added. The resulting dispersion was lyophilised and then redispersed in distilled water just prior to use.

Preparation 2

Perfluoromethylcyclobutane Emulsion

Hydrogenated phosphatidylserine (100 mg) in purified water (20 ml) was heated to 80° C. for 5 minutes and the resulting dispersion was cooled to 0° C. overnight. 1 ml of the dispersion was transferred to a 2 ml vial, to which was added 100 $\mu$l of perfluorodimethylcyclobutane (>97% 1,1-isomer, balance being 1,2- and 1,3-isomers). The vial was then shaken for 75 seconds using a CapMix® to yield an emulsion of diffusible component which was stored at 0° C. when not in use.

EXAMPLE 1

In vivo Imaging of Dog Heart with Perfluorobutane Gas Dispersion and Perfluorodimethylcyclobutane Emulsion and Coadministered Adenosine An occluding snare was placed around a major branch of the left anterior descending coronary artery of an open-chest 22 kg dog and an ultrasound transit time flowmeter was placed immediately downstream of the occluder, which was then adjusted to produce a steady 25% flow reduction from about 14 to 10 ml/min. The contents of three syringes, respectively containing (i) an amount of a perfluorobutane microbubble dispersion prepared as in Preparation 1 corresponding to 4.4 $\mu$l of gas content, (ii) an amount of the perfluorodimethylcyclobutane emulsion from Preparation 2 corresponding to 33 $\mu$l of the dispersed perfluorodimethylcyclobutane phase, and (iii) 3.0 mg adenosine dissolved in 0.9% saline, were then intravenously injected as a simultaneous bolus; commencing 10 seconds later a further 3.0 mg of adenosine dissolved in 0.9% saline was injected slowly over 20 seconds. Imaging of the left ventricle of the heart was performed using an ATL HDI-3000 scanner with a P5-3 probe; continuous ultrasonication at maximum power was applied for 1 minute to induce microbubble growth, whereafter the myocardium was examined using B-mode imaging. A clearly evident difference in gray scale levels could be seen between stenotic areas (brighter than baseline recordings) and normal areas (very much brighter than baseline recordings).

EXAMPLE 2

Comparative

The procedure of Example 1 was repeated, but without injection of adenosine. The differences in contrast intensity between areas supplied by normal and stenotic arteries were now only barely visible; the main difference from Example 1 was that the brightness of normal areas was reduced to a level closer to that of the regions supplied by the stenotic artery.

EXAMPLE 3

Imaging with Contrast Agent Under Dobutamine Stress

Example 1 was repeated except that a continuous infusion of dobutamine at a rate of 15 μg/kg/min was administered in place of adenosine. After a stable dobutamine effect consisting of an increase in heart rate from the normal 100 beats per minute to 150 beats per minute was obtained, the microbubble dispersion and the emulsion were intravenously injected from two syringes as a simultaneous bolus. Infusion of dobutamine was continued for another 2 minutes after the contrast agent injection. Towards the end of this period, a distinct pattern of myocardial contrast enhancement was seen, clearly depicting the areas supplied from the stenotic artery as darker than the normal myocardium. In addition, a myocardial contractility deficit consisting of a pronounced wall thinning was observed in the areas supplied by the stenotic artery.

What is claimed is:

1. A combined preparation for use as a contrast agent in ultrasound perfusion imaging, said preparation comprising:
    i) an ultrasound contrast agent which comprises:
        a) an injectable aqueous medium having gas dispersed therein, said dispersed gas being linked to one or more vectors having affinity for sites and/or structures within tissue microvasculature of a human or non-human animal subject; and
        b) a composition comprising a diffusible component, said diffusible component being separate from said dispersed gas and being capable, following administration of said contrast agent to said subject, of diffusion in vivo into said dispersed gas so as to promote controllable growth and temporary retention of said dispersed gas within tissue microvasculature in said subject at concentrations dependent on regional rates of perfusion within said tissue; and
    ii) a vasodilatation-inducing amount of a vasodilator drug.

2. A preparation as claimed in claim 1 wherein said vasodilator is a substance which is endogenous to said subject.

3. A preparation as claimed in claim 2 wherein said vasodilator drug is adenosine.

4. A preparation as claimed in claim 1 wherein said dispersed gas is linked to at least one vector having affinity for normal or activated endothelial cells.

5. A preparation as claimed in claim 1 wherein said dispersed gas is linked to at least one protein or peptide which binds to cell-surface proteoglycans.

6. A method of generating enhanced perfusion images of a human or non-human animal subject which comprises the steps of:
    i) injecting an ultrasound contrast agent which comprises:
        a) an injectable aqueous medium having gas dispersed therein, said dispersed gas being linked to one or more vectors having affinity for sites and/or structures within tissue microvasculature of a human or non-human animal subject; and
        b) a composition comprising a diffusible component, said diffusible component being separate from said dispersed gas and being capable, following administration of said contrast agent to said subject, of diffusion in vivo into said dispersed gas so as to promote controllable growth and temporary retention of said dispersed gas within tissue microvasculature in said subject at concentrations dependent on regional rates of perfusion within said tissue;
    ii) coadministering a vasodilatation-inducing amount of a vasodilator drug; and
    iii) generating an ultrasound image representing perfusion of a target organ or tissue.

7. A method as claimed in claim 6 wherein images representative of myocardial perfusion are generated.

* * * * *